(12) United States Patent
Griffiths et al.

(10) Patent No.: US 10,048,384 B2
(45) Date of Patent: Aug. 14, 2018

(54) METHODS AND SYSTEMS FOR TARGET MAPS FOR GOLF SHOTS

(71) Applicant: Shotzoom, LLC, Tempe, AZ (US)

(72) Inventors: Michael John Griffiths, Broomfield, CO (US); Benjamin David Addoms, Broomfield, CO (US)

( * ) Notice: Subject to any disclaimer, the term of this patent is extended or adjusted under 35 U.S.C. 154(b) by 263 days.

(21) Appl. No.: 14/795,691

(22) Filed: Jul. 9, 2015

(65) Prior Publication Data

US 2016/0008694 A1     Jan. 14, 2016

Related U.S. Application Data

(60) Provisional application No. 62/023,696, filed on Jul. 11, 2014.

(51) Int. Cl.

| | |
|---|---|
| A63B 69/36 | (2006.01) |
| G01S 19/19 | (2010.01) |
| G06F 19/00 | (2018.01) |
| H04M 1/725 | (2006.01) |

(52) U.S. Cl.
CPC .......... *G01S 19/19* (2013.01); *G06F 19/3481* (2013.01); *H04M 1/72544* (2013.01)

(58) Field of Classification Search
USPC ...................................... 463/16–42; 473/131
See application file for complete search history.

(56) References Cited

U.S. PATENT DOCUMENTS

| | | | | |
|---|---|---|---|---|
| 5,558,333 A | * | 9/1996 | Kelson | A63B 71/0669 463/1 |
| 5,882,269 A | * | 3/1999 | Lewis | A63B 69/3623 434/252 |
| 2009/0201263 A1 | * | 8/2009 | Hofmann | G06F 3/0488 345/173 |
| 2013/0063432 A1 | * | 3/2013 | Kaps | G06T 13/40 345/419 |
| 2015/0182836 A1 | * | 7/2015 | Freeman | G06K 9/00342 473/406 |

* cited by examiner

*Primary Examiner* — Masud Ahmed
(74) *Attorney, Agent, or Firm* — Brownstein Hyatt Farber Schreck, LLP

(57) ABSTRACT

This disclosure is directed to systems and methods for producing a target map for a computing device, such as a mobile device. A set of golf shot data may be obtained and may include shot location data from a plurality of users and associated with a hole on a golf course. A geographic region may be determined based on the shot location data. A subset of target locations may be calculated using a target score and the shot location data of the set of golf shot data. In some cases, the target score is par. A target map may be produced using the subset of target locations. A visual indicia of the target map may be displayed with an image depicting at least a portion of the hole on the golf course.

20 Claims, 14 Drawing Sheets

| | HANDICAP | GENDER | DATE | COURSE/ TEE BOX | TEE BOX | LANDING POSITION OF SHOT | SCORE ON HOLE | CLUB USED |
|---|---|---|---|---|---|---|---|---|
| GOLFER N | 18.4 | M | JULY 5 | NORTH COURSE/ WHITE | 2 | 39.9211427 LAT. -105.135151 LONG. | 4 PAR | DRIVER |
| GOLFER A | 2.3 | F | APRIL 12 | NORTH COURSE/ BLACK | 2 | 39.921231 LAT. -105.135769 LONG. | 3 BIRDIE | 3 WOOD |
| GOLFER Z | 12.5 | F | NOV. 12 | NORTH COURSE/ BLUE | 2 | 39.921179 LAT. -105.136431 LONG. | 4 PAR | 3 WOOD |
| GOLFER X | 21.3 | M | AUG. 7 | NORTH COURSE/ RED | 2 | 39.921165 LAT. -105.13599 LONG. | 5 BOGEY | DRIVER |
| ... | ... | ... | ... | ... | ... | ... | ... | ... |

FIG. 5

METHODS AND SYSTEMS FOR TARGET MAPS FOR GOLF SHOTS

CROSS-REFERENCE TO RELATED APPLICATION

This application is a non-provisional patent application of and claims the benefit to U.S. Provisional Patent Application No. 62/023,696, filed Jul. 11, 2014 and titled "Methods and Systems for Target Maps for Golf Shots," the disclosure of which is hereby incorporated herein by reference in its entirety.

TECHNICAL FIELD

Embodiments of this invention relate, generally, to computer-implemented golf applications, such as operating on mobile electronic devices or other types of devices.

BACKGROUND

In the game of golf, golfers have a variety of options when hitting a golf shot, including the type of golf club used (such as a driver, metal wood, hybrid, iron or wedge) to achieve a desired distance, and the target line for the shot (such as left side of the fairway, right of a bunker, cutting the corner on a dogleg fairway). These choices will vary depending upon the particular course being played, as well as the layout of the particular golf hole, fairway, hazards, and green, and course conditions (such as high wind or winter conditions).

As recognized by the present inventors, what is needed are computer-implemented methods, systems and devices for providing recommendations to a golfer relating to possible target zones to achieve greater success on a golf hole.

SUMMARY

According to one broad aspect of one embodiment of the present invention, disclosed herein are computer-implemented methods and systems for providing target zones (which can be in the form of target maps, target lines, or other visual indications of a target) for golfers on holes of various golf courses. The target maps can be formed based upon shot data collected from prior shot data including from other golfers who previously played the golf hole. The target zones may be used to indicate to the user locations on the golf course where shots were positioned that resulted in scores of par (or birdie or other results) with greater statistical frequency.

In this manner, embodiments of the present invention can aid a golfer in selecting a target, target zone or target line prior to the golfer executing a golf shot. In one example, embodiments of the present invention can aid a golfer in selecting a target, target zone or target line prior to the golfer executing the golfer's tee shot or any other shot for a particular golf hole on a particular golf course. In this way, embodiments of the present invention can help a golfer navigate a golf hole, help a golfer compare her or his shots to other golfers, help a golfer visualize how other golfers have played a golf hole, or otherwise enhance a golfer's enjoyment of the game of golf. Embodiments of the present invention can also be used by observers, golf instructors, course managers, and others to visualize how other golfers have played a golf hole, and the resulting scores that those golfers have achieved based on the positions/locations of their actual shots.

Some example embodiments are directed to a computer-implemented method of producing a target map for a computing system having a display, such as a mobile device. A set of golf shot data may be obtained, which includes shot location data from a plurality of users and associated with a hole on a golf course. The set of golf shot data may be obtained, for example, from a remote server via a computer network. A geographic region may be determined based on the shot location data. A subset of target locations may be calculated using a target score and the shot location data of the set of golf shot data. In some cases, the target score is par. A target map may be produced using the subset of target locations. A visual indicia of the target map may be displayed, using the display, with an image depicting at least a portion of the hole on the golf course.

In some embodiments, the visual indicia include a target line superimposed on the image. In some embodiments, the visual indicia include a percentage indication that corresponds to a statistical frequency of shots that resulted in the target score. Some embodiments include displaying a club selection based on the target map.

In some embodiments, a club selection is received from a user. A second subset of target locations may be determined that corresponds to shots performed using the club selection from the user. In some embodiments, a tee-box selection is received from a user. A second subset of target locations may be determined that corresponds to shots initiated from the tee-box selection from the user. In some embodiments, an adjusted target score is received from a user. An adjusted subset of target locations may be determined using the adjusted target score. An adjusted target map may be computed using the adjusted subset of target locations. In some embodiments, a handicap parameter is received from a user. A second subset of target locations may be determined using the handicap parameter.

Some example embodiments are directed to a computer server for producing a target map. The server may include a processor and a memory storing computer-readable instructions that, when executed by the processor, cause the mobile device to perform various functions. In some embodiments, the server may obtain a set of golf shot data from a database, the set of golf shot data including golf shot information from a plurality of users and associated with a hole on a golf course. The server may also determine a geographic region based on the golf shot information and calculate a subset of target locations based on a target score. A target map may be produced using the subset of target locations. The server may cause a display on a mobile device of a visual indicia of the target map overlaid on an image depicting at least a portion of the hole on the golf course.

In some embodiments, the server may be configured to communicate with a mobile device via a computer network. The mobile device may include a global positioning service (GPS) device for obtaining current location information. The set of golf data may include location information associated with previous shots. The golf data of the set of golf data may include one or more of: a number of shots for a hole; environmental conditions associated with a shot; and/or handicap information associated with a user. In some embodiments, the golf data has been collected using a shot tracking software application executed on a separate third-party mobile device. In some embodiments, the golf data was collected over multiple previous golf games and from multiple users.

Some example embodiments are directed to a computer-implemented method of producing a target map for a mobile device. A set of golf shot data may be obtained from a remote server via a computer network, the set of golf shot data may include golf shot information from a plurality of users and may be associated with a hole on a golf course. A filtered set of golf shot data may be computed by removing inaccurate data from the set of golf shot data. A subset of target locations may be determined using a target score, a club type, and the filtered set of golf shot data. The target score may be par or better or another score indicating the number of strokes. In some cases, the club type corresponds to a club used to drive from the tee-box on the current hole. In some cases, the club type corresponds to a club selected by the user for the current shot. A target map may be produced using the subset of target locations. The mobile device may display a visual indicia of the target map overlaid on an image depicting at least a portion of the hole on the golf course. In some embodiments, the visual indicia include a percentage indication that corresponds to a statistical frequency of shots that resulted in the target score. In some embodiments, the visual indicia include multiple target zones overlaid on the image.

Other embodiments of the disclosure are described herein. The features, utilities and advantages of various embodiments of this disclosure will be apparent from the following more particular description of embodiments as illustrated in the accompanying drawings.

BRIEF DESCRIPTION OF THE DRAWINGS

FIG. 5 illustrates examples of golf shot data that can be used in one example to provide recommended target shot locations for a golfer, in accordance with one embodiment of the present invention.

DETAILED DESCRIPTION

Disclosed herein are various embodiments of computer-implemented methods, systems and devices for providing target information, such as target zones, target lines, target regions, target maps, or other visual indications of a target, for golfers on holes of various golf courses. Target maps can be formed based upon shot data collected from golfers who previously played the golf hole, including an individual golfer and other golfers. In this manner, embodiments of the present invention can aid a golfer in selecting a target, target zone or target line prior to the golfer executing a golf shot—such as a tee shot, a second shot, an approach shot, a bunker shot, or other shots during play. Embodiments of the present invention can also be used by observers, golf instructors, course managers, and others to visualize how other golfers have played a golf hole, and the resulting scores that those golfers have achieved based on the positions/locations of their actual shots. Various embodiments of the present invention are disclosed herein.

Figure 1:
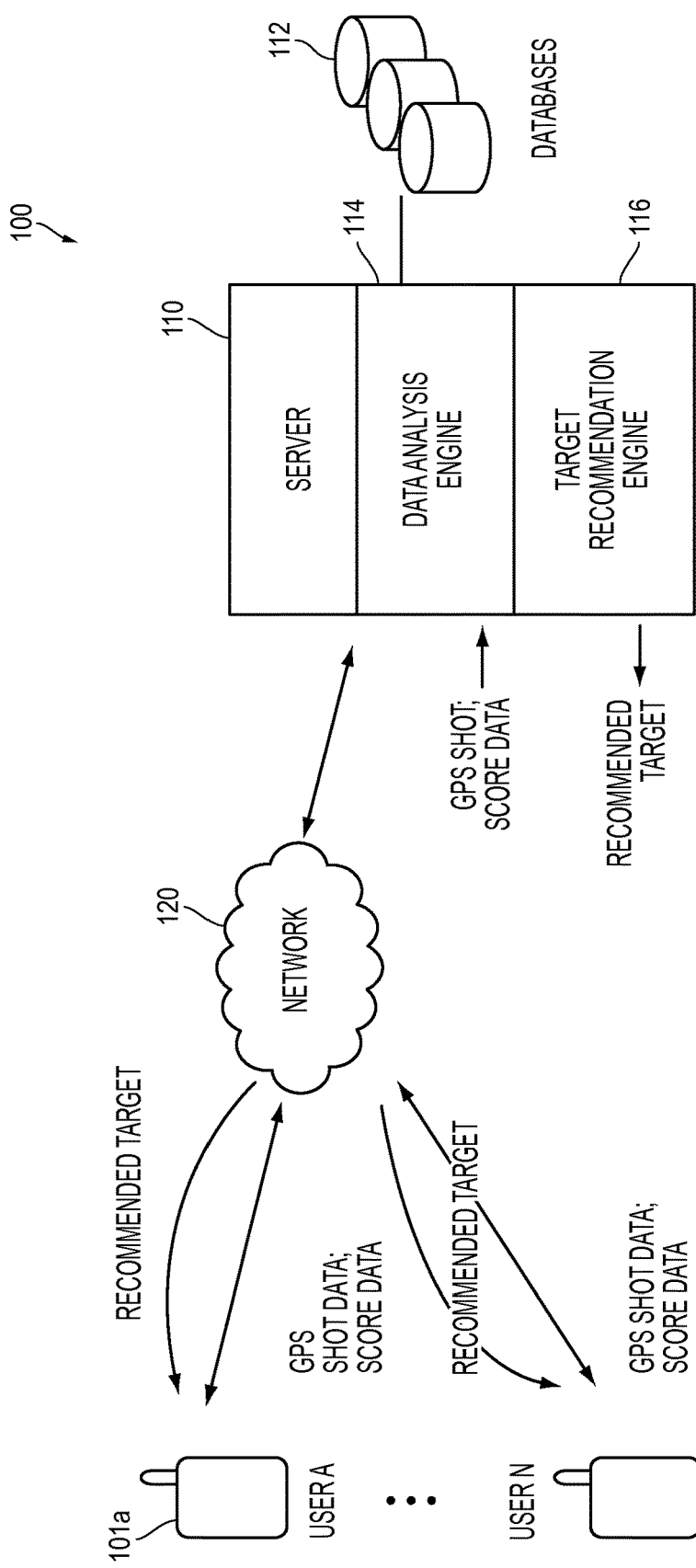
FIG. 1 illustrates an example of a block diagram of an example system for providing recommended target zones or shot locations for a golfer, in accordance with one embodiment of the present invention.

In FIG. 1, a block diagram is shown of an example system 100 and mobile devices 101a, 101b for providing recommended target shot locations for a golfer, in accordance with one embodiment of the present invention.

The mobile devices 101a, 101b may include a portable electronic device including a processor operably connected to computer memory (memory) that is used to store computer-readable or computer-executable instructions. The computer-readable or computer-executable instructions may include instructions for performing one or more of the operations or processes described herein with respect to various embodiments. The mobile devices 101a, 101b may also include one or more global positioning service (GPS) devices or other devices for obtaining location information of the mobile device. The mobile devices 101a, 101b may be one of a variety of different electronic devices including, for example, mobile phones, smart phones, tablet computers, GPS devices, golf range finders, or other mobile electronic devices. In some embodiments, a notebook computer, desktop computer, computer terminal, or other computing device having a display may be used instead of the mobile devices 101a, 101b depicted in FIG. 1. The mobile devices 101a, 101b may be utilized by users such as golfers, golf instructors, course managers and other observers, any of which may be generally referred to herein as "users."

As shown in FIG. 1, one or more computing devices (such as one or more servers 110) may be coupled with via a computer network 120, such as the Internet or other network, to communicate with one or more of the mobile devices 101a, 101b. The server 110 may include or be coupled with one or more databases 112, wherein the databases store or provide access to prior golf shot data of the plurality of golfers on holes of a plurality of golf courses. An example of the types of data that may be stored in the databases 112 or accessible to the server 110 is provided in FIG. 5, described below.

The databases 112 may include golf shot data including, for example, geolocation shot data (such as shot location data), score data, season data, environmental conditions, handicap information, and other items of data, for a variety of golfers that have played the various holes of a variety of golf courses, including prior shot data from the individual golfer who is using the system if that individual previously played the same golf hole. The golf shot data may be communicated to the server 110 and/or the mobile devices 101a, 101b on request. The golf shot data may be communicated as part of a set of golf shot data that may be associated with a golf course, hole on a golf course, or other region of interest.

The golf shot data may be collected using the mobile devices 101a, 101b and stored in the databases 112. For example, the golf shot data may be collected by a mobile device 101a, 101b utilized by a golfer during a round of golf, such as through an application computer program running on a golfer's mobile device which tracks golf shot data of the golfer while the golfer is playing the round of golf. In some instances, geolocation data may be collected using a global positioning service (GPS) device, cellular network locations services, or other device locating system. The data collection may be performed by a shot tracker or golf-based software that runs on a golfer's smart phone. Embodiments of the present invention may utilize golf shot data that may be stored in the databases or otherwise accessible to the server which originated from an application computer program, such as a shot tracking computer application program.

In one example, the server/computing device 110 include a data analysis engine 114 which analyzes golf shot data, golf score data and other data; and a target recommendation engine 116 which generates a recommended target zone, target line, target map, or other indications of targets for golfers on holes of a golf course.

In one example, the data analysis engine 114 and the target recommendation engine 116 may operate on the server/computing device 110, and these engines may implement one or more of the operations, processes, functions, or features described herein. In some embodiments, the mobile devices 101a, 101b perform one or more of the operations, processes, functions, or features described herein either alone or in combination with the data analysis engine 114 and the target recommendation engine 116. That is, the data analysis engine 114 and/or recommendation engine 116 may reside on the server 110 and/or the mobile devices 101a, 101b.

Embodiments of the present invention will be described with reference to providing target maps, target zones, target lines, or other indications of targets, for use by a golfer in hitting tee shots for a golf hole. It should be understood that embodiments of the present invention can also be utilized for providing targets for other shots during a round of golf, as desired, such as a second shot, an approach shot, a bunker shot, or other shots during play.

Figure 2:
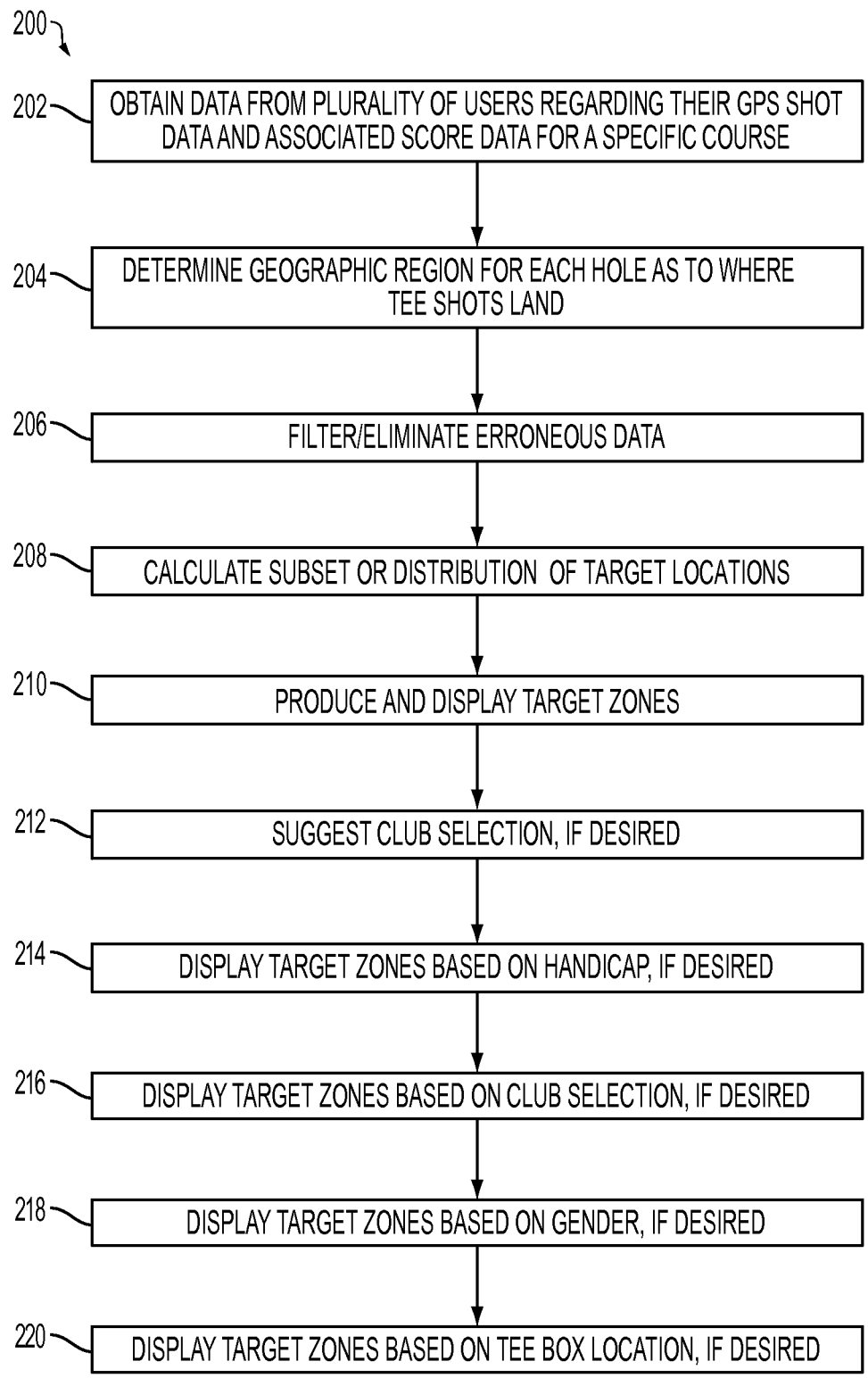
FIG. 2 illustrates an example of a process for providing target shot location maps for a golfer, in accordance with one embodiment of the present invention.

FIG. 2 depicts an example process 200 for providing target shot location maps for a golfer, in accordance with one embodiment of the present invention. One or more of the operations of process 200 may be performed, for example, using a computing device, such as the server 110 and/or mobile devices 101a, 101b described above with respect to FIG. 1. In particular, the operations of process 200 may be embodied in computer-readable or computer-executable instructions that are executed by a processor(s) of the server 110 and/or mobile devices 101a, 101b.

At operation 202, golf shot data is obtained from multiple users. The golf shot data may include geolocation data shot locations for a specific golf course, golf hole or other region of interest. The golf shot data may be collected over a series of previous games from one user or from multiple users. In one example, operation 202 may include obtaining geolocation data, score data, golf club data, season data, environmental condition data, and other data associated with one or more holes of a golf course. With respect to some of the examples provided herein, the golf shot data may be associated with a tee-shot for a hole of the golf course. However, the golf shot data may be associated with any other type of shot and is not necessarily limited to the tee-shot examples provided herein.

Operation 202 may obtain the golf shot data from application computer programs that track golf shot data, such as shot tracking computer application programs that run on a golfer's smart phone, electronic yardage device, notebook computer or other computing device. A GPS device, cellular network location service, or other system for obtaining the device location may be used to collect geolocation data associated with one or more golf shots. In one example, a database may store such golf shot data, and the golf shot data stored in the database may have been collected over months or years of prior play by golfers. An example of the types of data that may be stored in the databases is provided in FIG. 5, described below. Thus, the obtaining operation 202 may include obtaining previously collected and stored golf shot data that is stored on a database. The golf shot data may be obtained from a remote server or other computer via a computer network. The golf shot data may also be obtained from computer memory, whether internal or externally provided by a removable computer-readable storage medium.

In one example, operation 202 obtains prior golf shot data for a particular hole of a golf course in order to formulate the target zones, target map, target line, or other indication of a target for a golfer. This operation may be performed, for example, in response to a request from a server (e.g., server 110, FIG. 1) and/or a mobile device (e.g., mobile device 101a, 101b of FIG. 1.)

At operation 204, for a given golf hole, a geographic region may be determined, wherein the geographic region defines a region as to where tee shots have landed based on the golf shot data obtained by operation 202. The geographic region may be determined based on the shot location data of the golf shot data obtained by operation 202. The shot location data may include, for example, coordinates of locations where a ball has landed on the course after being shot from a previous location, such as the tee-box. In some cases, the shot location data corresponds to the location where the next shot was shot from, which may be assumed to be the same location as where the ball landed from the previous shot. The shot location data may include GPS coordinates or other location-based information.

The geographic regions determined in operation 204 may correspond to a region in which some or all of the tee shots have landed from a particular location, such as the tee-box. In some embodiments of operation 204, multiple geographic regions are determined. Each geographic region may correspond to a grouping of shot locations that are in proximity to each other.

At operation 206, for a given golf hole, the shot data obtained by operation 202 may be filtered to eliminate inaccurate data and produce a filtered set of golf shot data. The inaccurate data may also be characterized as bad or erroneous data. Such inaccurate data may be the result of GPS errors, software errors, data errors, operator errors or other reasons. For instance, if the prior golf shot data includes data that is invalid or out of the extent or bounds of the golf course, such data may be filtered out. In some cases, operation 206 eliminates inaccurate data that corresponds to outlier data. For example, operation 206 may eliminate data that is associated with a shot that is too far away from other shots in the set of golf shot data. In some cases, a number of standard deviations of shot location data, weighted average, or other statistical measurement of the golf shot data is used to eliminate inaccurate or bad data.

Operation 206 may be used to produce a filtered set of golf shot data that is then used to determine or produce a target map for the hole. In some cases, operation 206 is performed before operation 204. In some cases, operation 206 may be performed after one of the operations described below. In some cases, operation 206 may not be performed and may be omitted from process 200.

At operation 208, based on the prior golf shot data, subsets and/or distributions can be calculated as to where prior golf shots were located on the fairway or green. Operation 208 may also include calculating a subset of target locations by using a target score and the shot location data of the (filtered) golf shot data. The subset of target locations may include location data associated with previous shots that satisfies a target score criteria. The target score may be set by the system or may be obtained from the user as a user input or user setting. In some cases, the subset of target locations is determined using one or more other criteria including, for example, club type, handicap, environmental conditions, player characteristic, and so on. The subset of target locations may be generally referred to as a distribution of target locations and may correspond to a region or area.

In one example, the locations of shots that resulted in a desired score (i.e., par or better) are collected, and other filters or variables may be accounted for as described herein. In one example, the distributions/averages calculated are correlated to a particular desired score for the golf hole, such as par, birdie, eagle, bogey, double bogey, or other result. In one example, if a golfer has requested target zones for a golf hole that resulted in a score of par or better, then operation 208 may filter the golf shot data so as to focus on golf shot data where the prior golfer achieved a score of par or better.

As described in more detail below with respect to FIGS. 5-9, a subset of target locations may be determined based on various other criteria associated with the golf shot data. Additional criteria include, for example, selecting and/or omitting golf shot data associated with a particular season (e.g., summer, fall, wet, dry). The subset of target locations may also be determined based on handicap, club type, gender, tee-box, and so on. In some implementations, the user may select multiple criteria that are used to determine the subset of target locations. The subset of target locations may also be computed over multiple iterations, each iteration applying one or more additional criteria.

At operation 210, a target map including, for example, target regions, target zones, and/or target lines may be computed, produced, or created based upon the golf shot data, subset of target locations, and/or distributions/averages calculated at operation 208. The target map may represent a region, area, or boundary on the golf course that corresponds to an area that includes some or all of the subset of target locations of operation 208. The subset of target locations may be further filtered and/or processed to produce the target map of operation 210.

As part of operation 210, a visual indicia of the target map may be displayed or caused to be displayed on a mobile device. For example, a target map, including target regions, target zones, and/or target lines may be superimposed onto an image of the fairway or green of a particular golf hole. In some embodiments, the visual indicia include a bounded area and/or a percentage indication that corresponds to a statistical frequency of shots that resulted in the target score.

Figure 3:
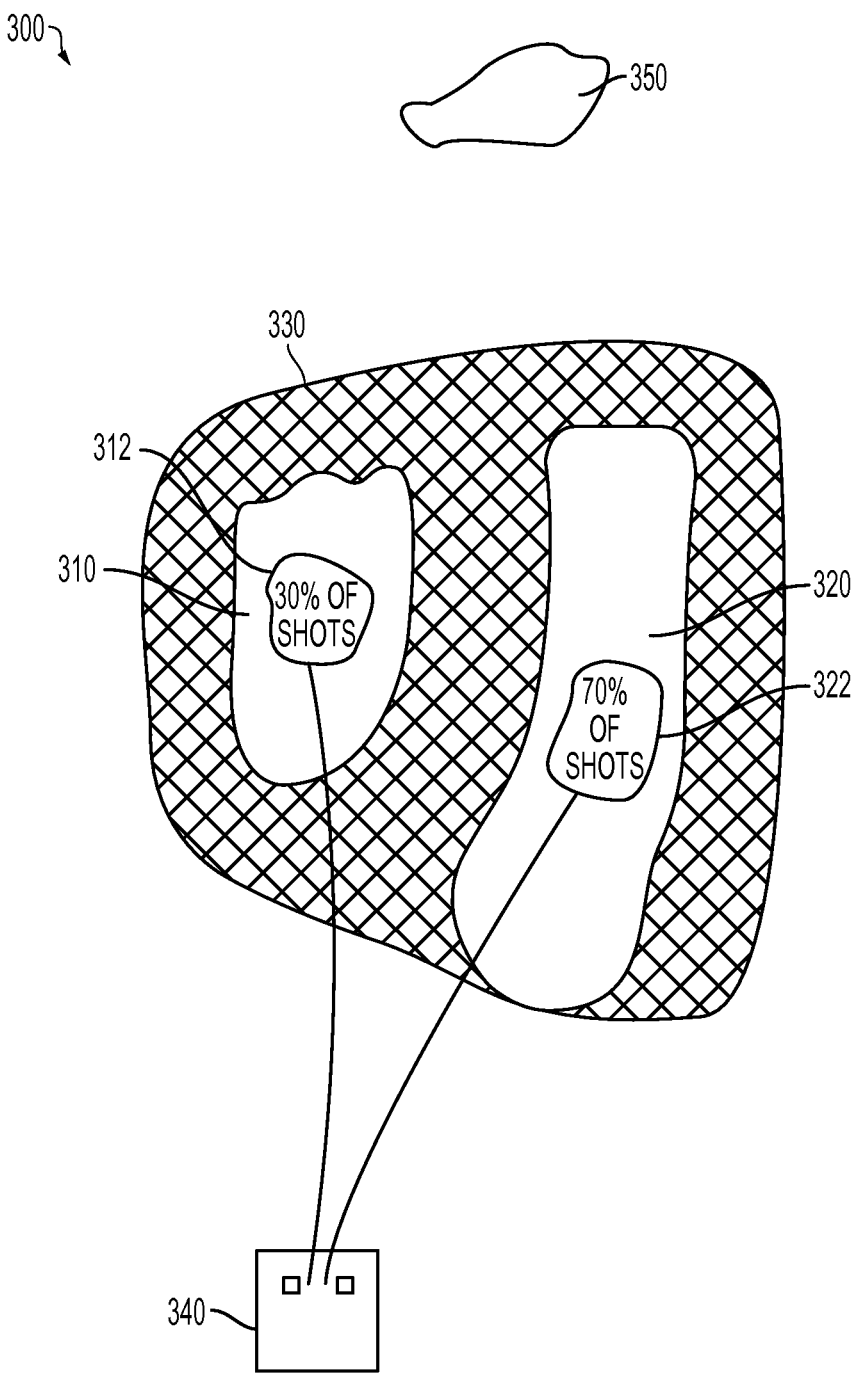
FIG. 3 illustrates an example of a graphical user interface of an electronic device showing target information based on prior golf shot data, in accordance with one embodiment of the present invention.
Figure 4:
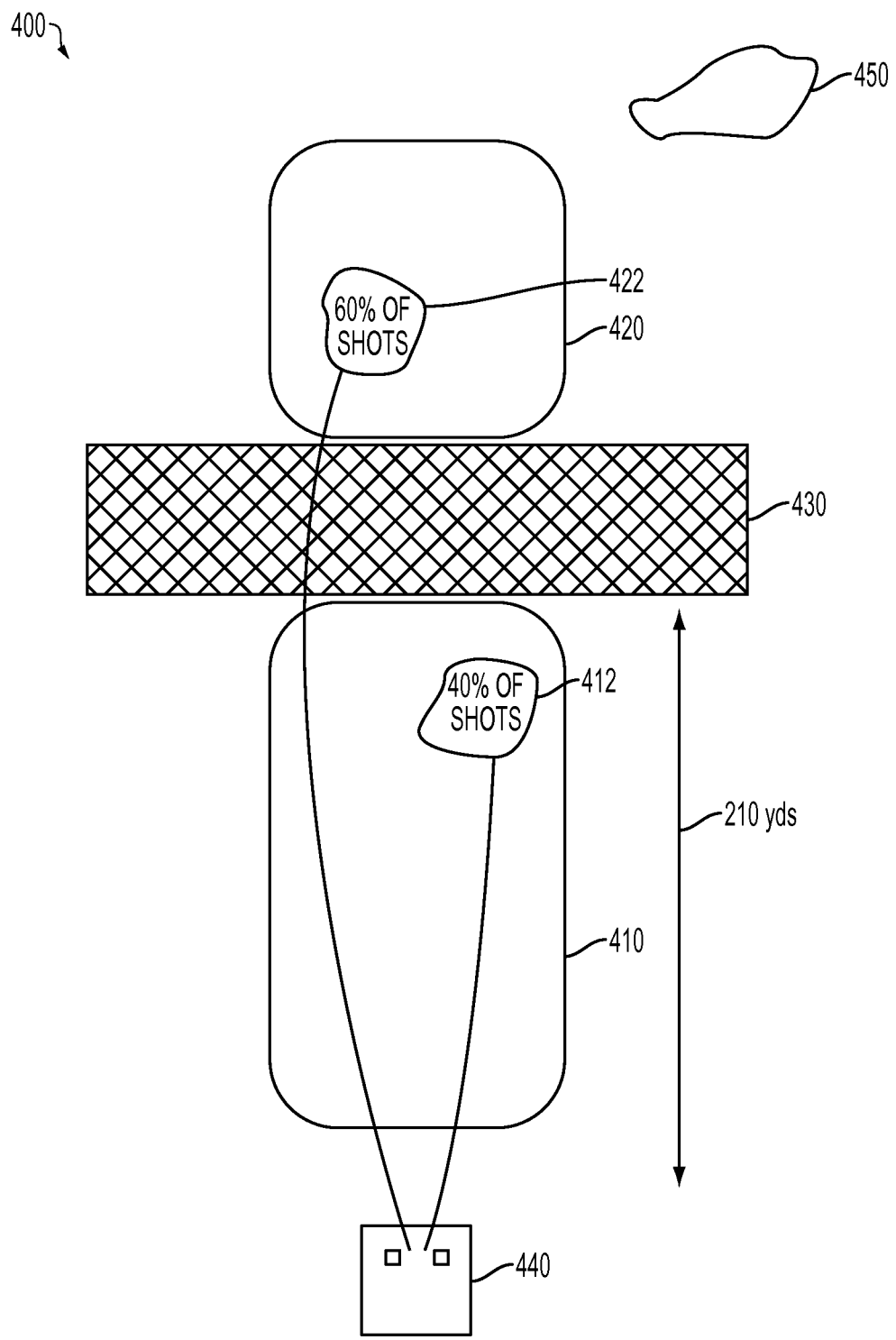
FIG. 4 illustrates another example of a graphical user interface of an electronic device showing target information based on prior golf shot data, in accordance with one embodiment of the present invention.

The visual indicia of the target zones may be superimposed or overlaid on an image of the fairway or green at the corresponding or appropriate locations. The image may be an overhead image obtained using a satellite or other overhead imaging system. FIGS. 3-4 illustrate various examples of target maps including target regions, target zones, and/or target lines that may be created by operation 210. These target maps may be displayed to a user to indicate to the user the locations on the golf course where scores of par (or birdie or other results) are achieved with greater statistical frequency. Other examples of operations 202-210 are described with reference to FIGS. 10-13 herein.

At operation 212, a club suggestion may be provided or displayed. For instance, if 60% of golfers that achieved par on a golf hole on a particular target zone utilize a 3 wood to hit the golf shot, such club suggestion may be indicated to the user.

Figure 6:
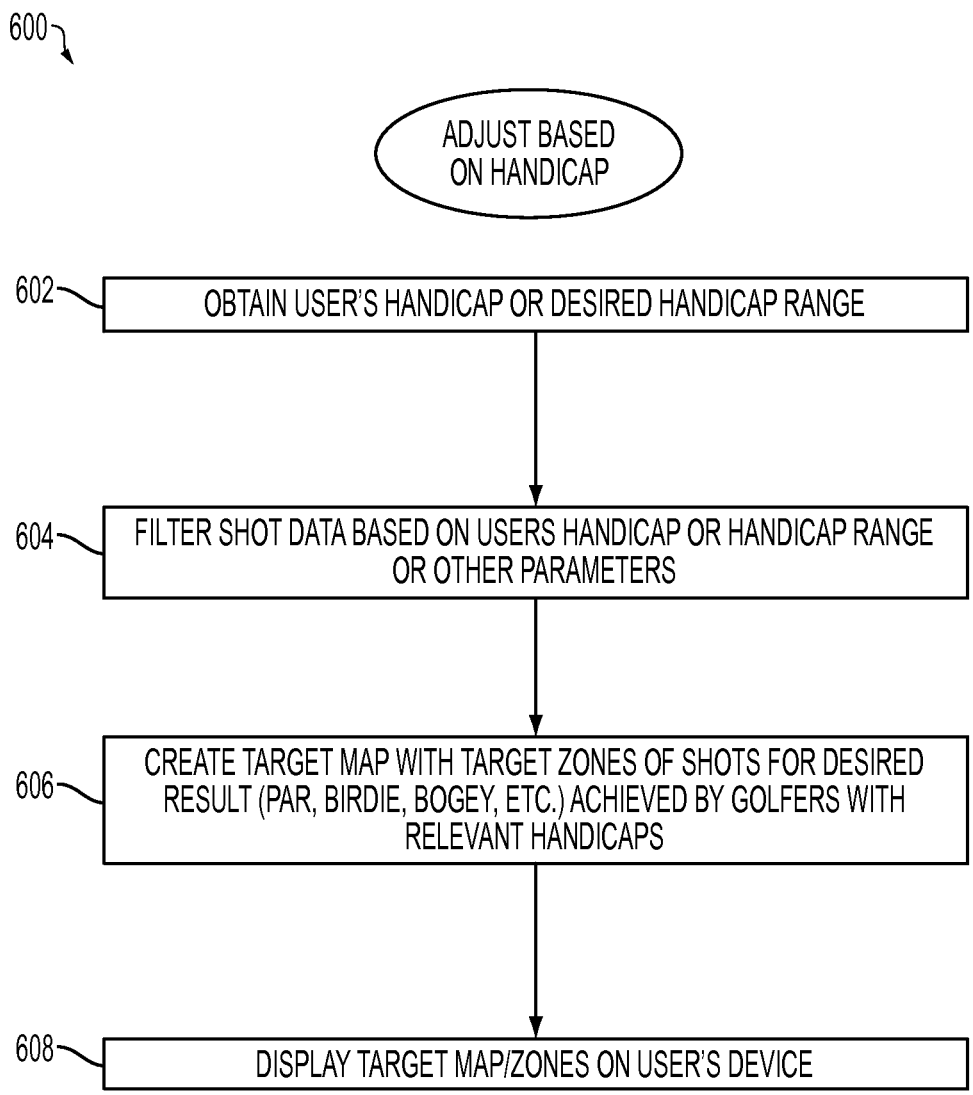
FIG. 6 illustrates an example of a process for providing target shot location data for a golfer, utilizing handicap information, in accordance with one embodiment of the present invention.

At operation 214, the target zones, target lines, target maps, and other target data may be adjusted based upon various factors or filters, if desired, such as by factors including but not limited to handicap information, club selection, gender, and tee-box. For instance, a golfer or other user may wish to view target zones based on prior golf shots by golfers with comparable handicaps. In one example, a scratch golfer with a zero handicap may request to see target zones/target maps for golfers of comparable handicaps that achieved a score of birdie or better on a golf hole. These target zones/target maps may be significantly different than those that include data related to golfers with higher handicaps, in one example. In this manner, operation 214 provides a user with the ability to visualize how other golfers with differing skill levels have played a golf hole, as well as the resulting outcomes that those golfers achieved on the golf hole. FIG. 6 provides additional operations that may be performed in another embodiment of the present disclosure related to operation 214.

Figure 7:
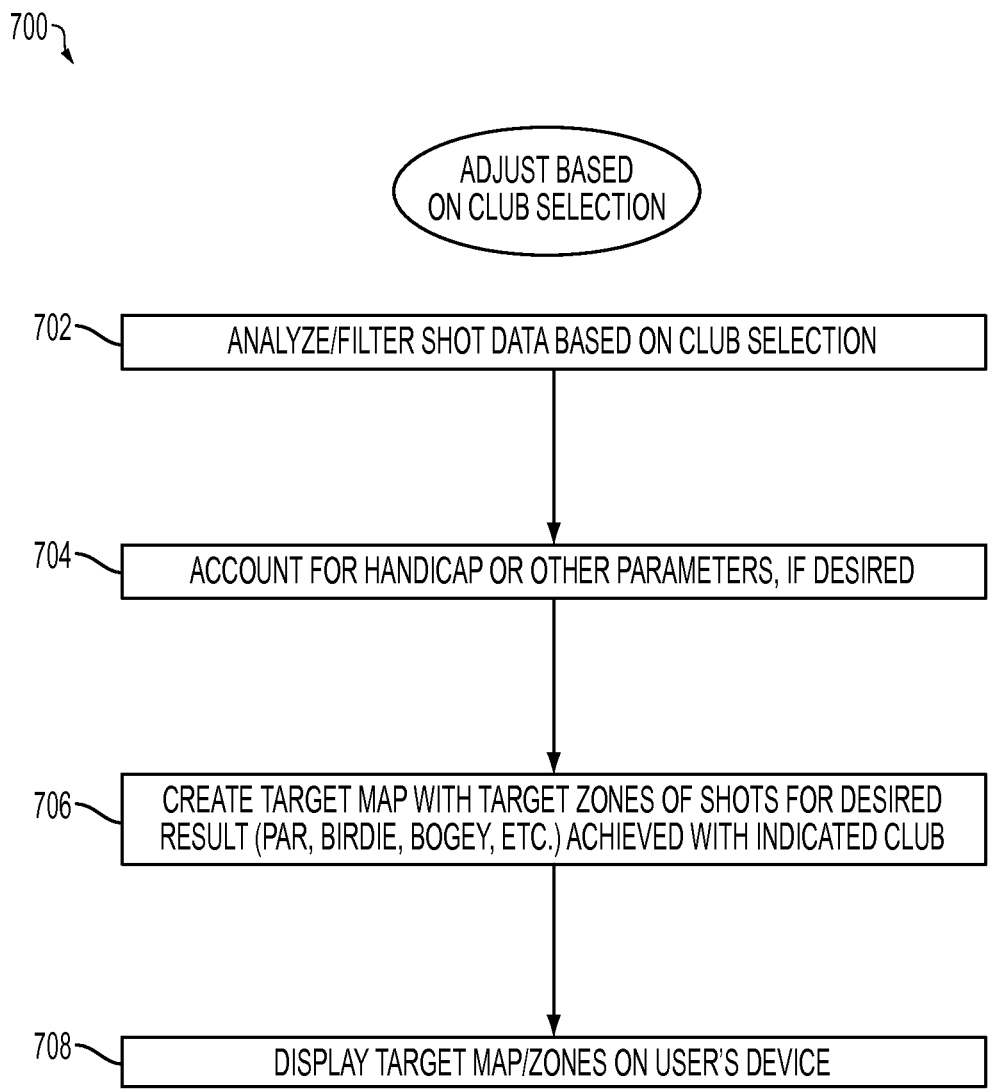
FIG. 7 illustrates an example of a process for providing target shot location data for a golfer, utilizing club selection information, in accordance with one embodiment of the present invention.

In another example, a golfer or other user may wish to view target zones based on prior golf shots by golfers using a particular golf club. In one example, a golfer playing a par 3 hole from the blue tees may request to see target zones/target maps for golfers that played the hole using a 2-iron versus a 3-iron. A club selection may be received from the user or a user setting and used to determine a second or refined subset of target locations that are used to generate the target zone(s). In this manner, operation 216 provides a user with the ability to visualize how other golfers using differing clubs have played a golf hole, as well as the resulting outcomes that those golfers achieved on the golf hole. FIG. 7 provides additional operations that may be performed in another embodiment of the present disclosure related to operation 216.

Figure 8:
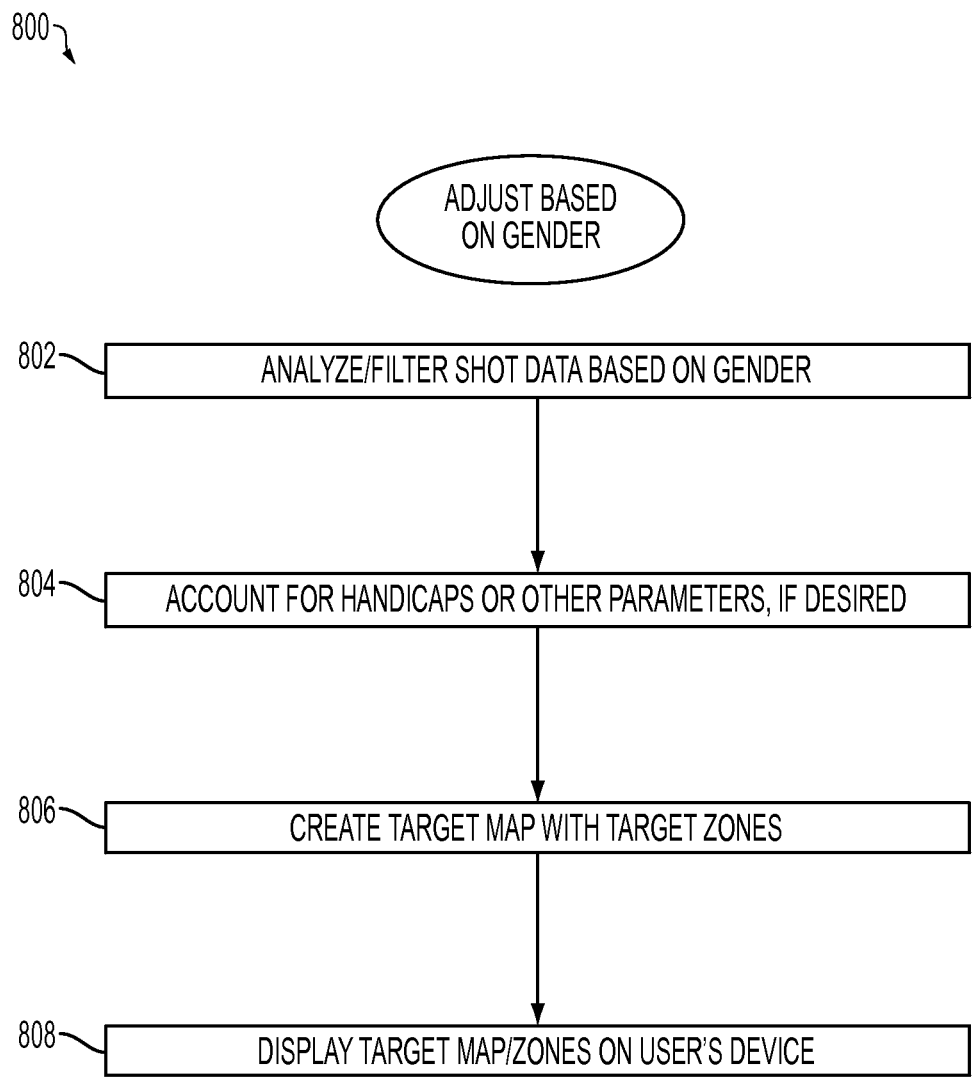
FIG. 8 illustrates an example of a process for providing target shot location data for a golfer, utilizing a filter based on gender, in accordance with one embodiment of the present invention.

In another example, a golfer or other user may wish to view target zones based on prior golf shots by golfers of the same gender (male or female). In one example, a female golfer may request to see target zones/lines/target maps for other female golfers that played the hole. In this manner, operation 218 provides a user with the ability to visualize how other golfers of the same gender have played a golf hole, as well as the resulting outcomes that those golfers achieved on the golf hole. FIG. 8 provides additional operations that may be performed in another embodiment of the present invention, related to operation 218.

Figure 9:
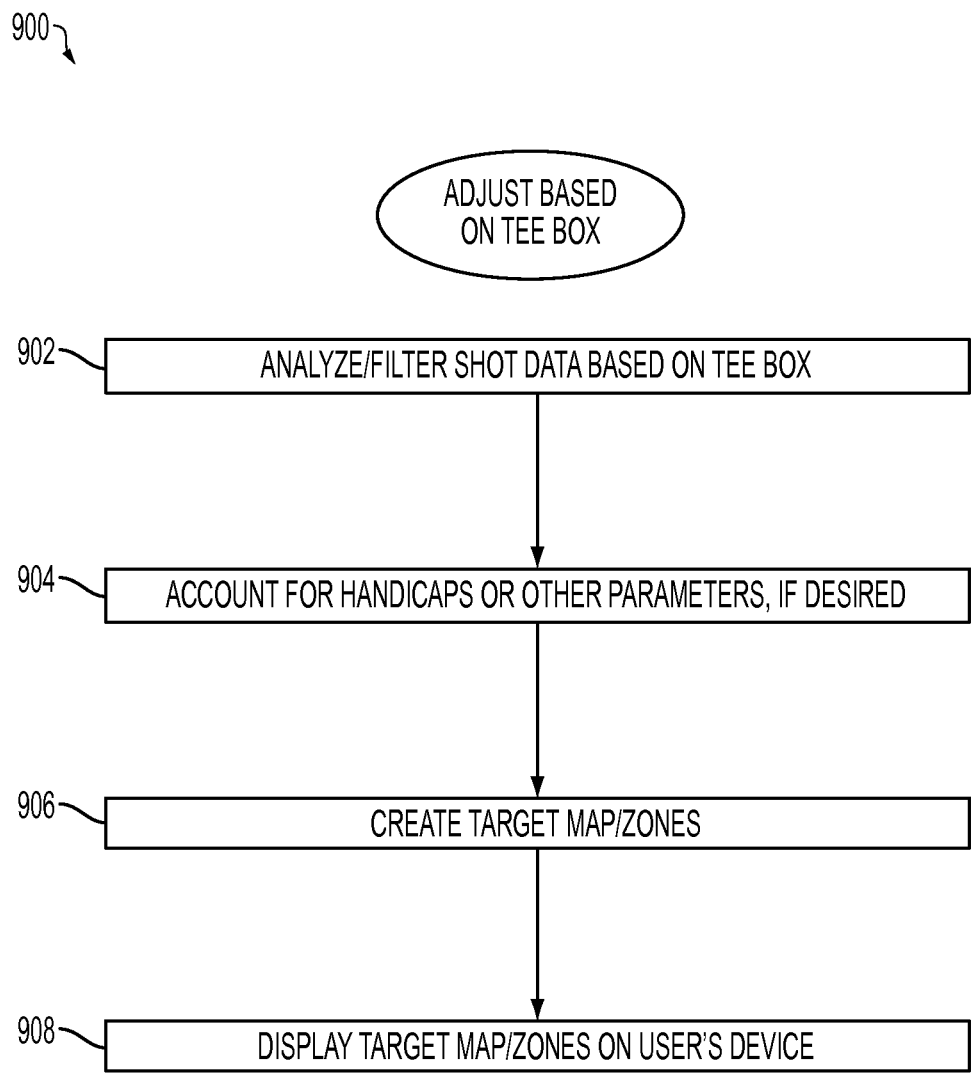
FIG. 9 illustrates an example of a process for providing target shot location data for a golfer, utilizing a filter based on tee-box location, in accordance with one embodiment of the present invention.

In another example, a golfer or other user may wish to view target zones based on prior golf shots by golfers that hit from a particular tee-box. In one example, a golfer playing a par 3 hole from the blue tees may request to see target zones/lines/target maps for golfers that played the hole from the blue tees. In this manner, operation 220 provides a user with the ability to visualize how other golfers have played a golf hole from a particular tee-box of the golf hole, as well as the resulting outcomes that those golfers achieved on the golf hole. FIG. 9 provides additional operations that may be performed in another embodiment of the present invention, related to operation 220.

In addition to the examples provided above, the user may provide an adjusted target score which is used to generate an adjusted subset of target locations. The adjusted subset of target locations may be used to generate an updated or adjusted target zone(s) which is displayed or presented to the user. For example, an initial set of indicia for a set of target zones may be displayed that correspond to a target score of par. The user may then request an updated or adjusted target zone(s) that is computed based on a target score of −1 par or birdie.

FIGS. 3-4 illustrate examples of graphical user interfaces of an electronic device showing target information based on prior golf shot data, in accordance with one embodiment of the present invention. In this example, the graphical user interface includes an overhead image of a golf hole 300, which may include a digital photograph or other graphical representation of the actual hole being played by the user. In the example of FIG. 3, a golf hole 300 has a split fairway with a first fairway 310 and a second fairway 320 surrounded by hazards 330. The hole 300 also include the location of the tee-box 340 and the location of the green 350.

The display of FIG. 3 includes visual indicia for two target zones: a first target zone 312 that corresponds to a location on the first fairway 310, and a second target zone 322 that corresponds to a location on the second fairway 320. In the present example, the target zones include a bounded area and a percentage indication associated with that area. In particular, as calculated by an embodiment of the present invention, 30% of the pars achieved on this hole had shots that landed within the target zone 312 indicated within the first fairway 310; and 70% of the pars achieved on this hole tee had shots that landed in the second target zone 322 indicated within the second fairway 320. While target zones 312, 322 are depicted as regions or areas, a target line or other visual indicia could also be used. The example of FIG. 3 illustrates how embodiments of the present invention can aid a golfer in determining where to aim the tee shots (i.e., whether to aim for the first fairway or the second fairway) in order to improve the chances of achieving a score of par.

FIG. 4 depicts another example hole 400 having a first fairway 410, second fairway 420, hazard 430, tee-box 440, and green 450. In the example of FIG. 4, the golf hole 400 has a split fairway with a first fairway 410 that terminates into a hazard 430, and a second fairway 420 that is beyond the hazard 430 but closer to the green 450. In this example, the graphical user interface of FIG. 4 shows that, as calculated by an embodiment of the present invention, 60% of the pars achieved on this hole had shots that landed in the target zone 422 indicated within the second distant fairway; and 40% of the pars achieved in this hole had shots that landed in the target zone 412 indicated within the first fairway 410. While target zones 412, 422 are depicted as regions or areas, a target line or other visual indicia could also be used. The example of FIG. 4 illustrates how embodiments of the present invention can aid a golfer in determining where to aim tee shots (i.e., whether to play a layup shot in the first fairway short of the hazard, or whether to attempt to hit the tee shot over the hazard onto the second portion of the fairway) in order to improve their chances of achieving a score of par.

FIG. 5 illustrates examples of golf shot data that can be used in one example to provide recommended target zone for a golfer, in accordance with one embodiment of the present invention. In one example, such data as shown in FIG. 5 may be stored in the one or more databases 112 shown in FIG. 1, or may otherwise be accessible to computing device/servers 110 shown in FIG. 1. It is understood that the data shown in FIG. 5 is provided by way of example only, and that embodiments of the invention could utilize other formats and types of data if desired.

In one example, the golf shot data may include, for each golfer that has played a particular golf hole on a particular golf course: an identification of the golfer (such as a user id number or other value), the golfer's handicap (such as the golfer's handicap index), the golfer's gender (male/female), the date the golfer played the golf course, the tee-box from which the golfer played a golf hole, the position or location of the shot as measured by the golfer's GPS enabled device (wherein in one example, the landing position of the shot is the shot position after the carry and roll of the shot), the golfer's score on the golf hole, and the club used by the golfer to execute the golf shot if desired. Other data may be used if desired, such as the golfer's age and other data related to course conditions or playing conditions may also be tracked and stored in the database—such as but not limited to wind speed, wind direction, temperature, barometric pressure, season (e.g., spring, summer, fall, winter, dry, wet). Such data may be entered manually by a user or automatically tracked by the device. In one example, prior golf shot data that occurred during play in similar conditions can be used to provide or formulate the target zones described herein.

In one example, prior golf shot data associated with differing conditions can be excluded from the determination of target zones. For instance, golf shot data from winter season or non-summer play may be excluded from the set of golf shot data used to compute or determine the target map for a user that is playing a golf round in the summer season.

For instance, as shown in the example of FIG. 5, Golfer N has a handicap of 18.4 and played from the White tees and scored 4 (par) using a driver for the tee shot. Golfer A has a handicap of 2.3 and played from the Black tees and scored 3 (birdie) using a 3-wood for the tee shot. Golfer Z has a handicap of 12.5 and played from the Blue tees and scored 4 (par) using a 3-wood for the tee shot. Golfer X has a handicap of 21.3 and played from the Red tees and scored 5 (bogey) using a driver for the tee shot.

It can be seen that for the example data of FIG. 5 various analysis can be made by the data analysis engine 114 of FIG. 1, such as determining a target zone based on prior golf shot data that accounts for a golfer's handicap, gender the resulting score, the tee-box played from, or the type of golf club used to hit the tee shot.

FIG. 6 illustrates an example of a process 600 for providing target shot location data for a golfer, utilizing handicap information, in accordance with one embodiment of the present invention. At operation 602, a player's handicap or desired handicap range is obtained. For instance, if a user desires to receive a target zone utilized by scratch golfers, then a user may input such information into a graphical user interface for instance. Alternatively, if a user desires to visualize a target zone utilized by bid handicap players with handicaps of 10 to 15, such information may be input or requested by the user. In another example, the user's handicap is obtained, and for each golf hole, the target zones or target maps are automatically calculated to include the shots hit by golfers of the same or similar handicaps.

At operation 604, the golf shot data is filtered based upon the handicap or handicap range specified by operation 602. The golf shot filtering may be performed in accordance with operation 208 and or 206 described above with respect to process 200. In particular, a second subset of target locations may be determined that correspond to the obtained handicap.

At operation 606, a target map or target zones of the golf shots for the desired result (such as par, birdie, bogey, etc.) is created based on the golf shot data from golfers having the relevant handicaps obtained by operation 602. In this manner, the operations of FIG. 6 can be utilized by embodiments of the present invention to adjust the target zones or target maps based on a particular handicap or handicap range. Operation 608 displays the target zones or maps, as desired by the user.

FIG. 7 illustrates an example of a process 700 for providing target golf shot location data for a golfer, utilizing club selection information, in accordance with one embodiment of the present invention. For instance, in one example, a user may want to display target zones of players that scored par or better utilizing a driver from the tee-box, and then a user may want to display target zones of players that scored par or better utilizing a 3-wood from the tee-box. A club selection may be received from the user or otherwise obtained.

At operation 702, the prior shot data is analyzed based upon the club selection indicated by the user. Operation 702 may be performed in accordance with operation 208 and/or 206 described above with respect to process 200. In particular, a second subset of target locations may be determined that correspond to golf shots performed using the club selection from the user or otherwise obtained.

At operation 704, if desired, handicap information can be accounted for in the data analysis. For instance, if the user desires to see the target zone data from prior golf shot data of players having a handicap index in the range of 0 to 5, the analysis can be adjusted accordingly. At operation 706, a target map of the shots for the desired results (such as par, birdie, bogey, etc.) is created as achieved by the particular club indicated or selected by the user at operation 702. Operation 708 displays the target zones or maps, for instance as desired by the user.

FIG. 8 illustrates an example of a process 800 for providing target shot location data for a golfer, utilizing gender information, in accordance with one embodiment of the present invention. For instance, in one example, a user may want to display target zones of male or female players that scored par or better from the tee-box. The gender of the user, or other player characteristic, may be received from the user or otherwise obtained.

At operation 802, the prior shot data is analyzed based upon the gender of the golfer in accordance with the filtering/subset generation techniques described herein. At operation 804, gender information can be accounted for in the data analysis. For instance, if the user desires to see the target zone data from prior golf shot data of other female players, the analysis can be adjusted accordingly. At operation 806, a target map of the shots for the desired results (such as par, birdie, bogey, etc.) for players of the gender selected by the user at operation 802 is created and displayed to the user. Operation 808 displays the target zones or maps, for instance, as desired by the user.

FIG. 9 illustrates an example of a process 900 for providing target shot location data for a golfer, utilizing information filtered by tee-box selection, in accordance with one embodiment of the present invention. For instance, in one example, a user may want to display target zones of players that scored par or better from the white tee-box of a particular golf hole. A tee-box selection may be received from the user or otherwise obtained.

At operation 902, the prior golf shot data is analyzed based upon the tee-box selected by the user in accordance with the filtering/subset generation techniques described herein. At operation 904, tee-box information can be accounted for in the data analysis. For instance, if the user desires to see the target zone data from prior golf shot data of other players from the white tee-box, the analysis can be adjusted accordingly. At operation 906, a target map of the shots for the desired results (such as par, birdie, bogey, etc.) for players from the tee-box selected by the user at operation 902 is created and displayed to the user. Operation 908 displays the target zones or maps, for instance, as desired by the user.

Target zones may also be created based on other variables, such as the pin position on a hole. In one example, the prior golf shot data can be analyzed to determine the corresponding pin position of a hole as played by a prior golfer, and the target zones presented to a user can account for such pin positions. For instance, on a par 3 hole, the prior golf shot data can be analyzed to determine if the pin was on the left, middle or right of the green. Then, depending upon the pin location of the par 3 hole that the user is playing, the prior golf shot data that corresponds to the same or similar pin position can be used by the system in determining the target zones to present to the user. In this way, the accuracy of the target zones can be improved based upon pin positions.

Figure 10:
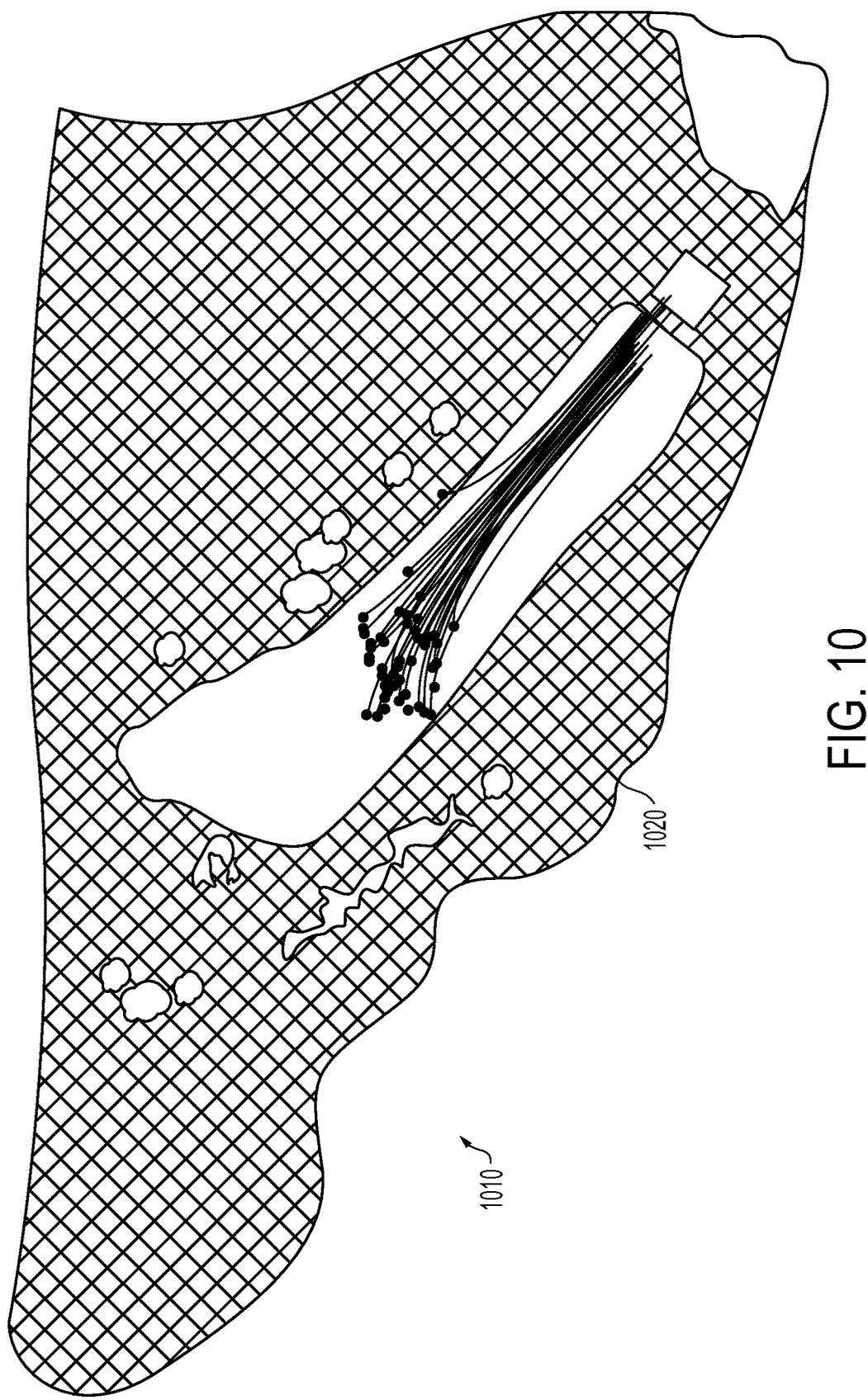
FIGS. 10-13 show various examples of golf course holes with shot data superimposed thereon, in accordance with some embodiments of the present invention.
Figure 11:
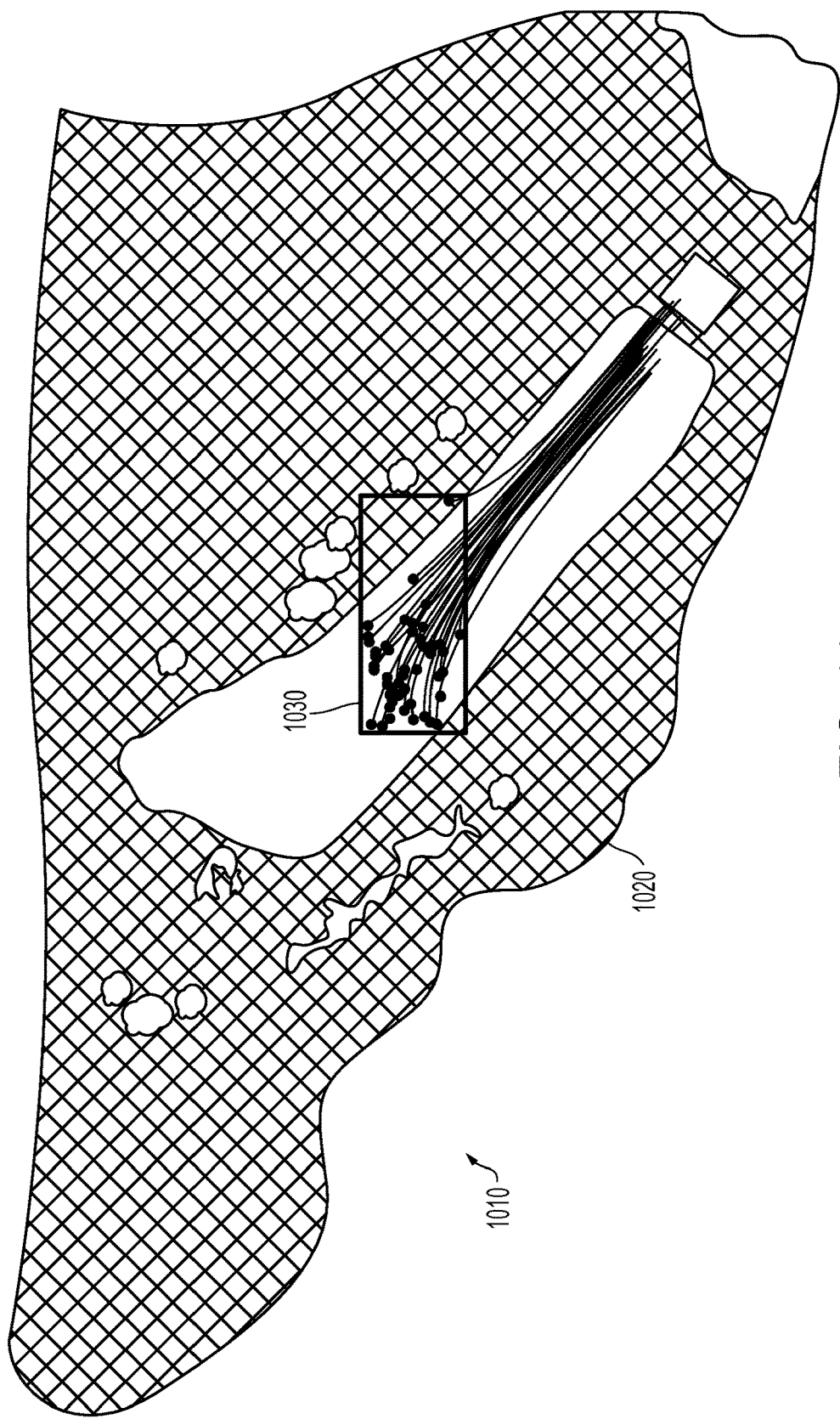
Figure 12:
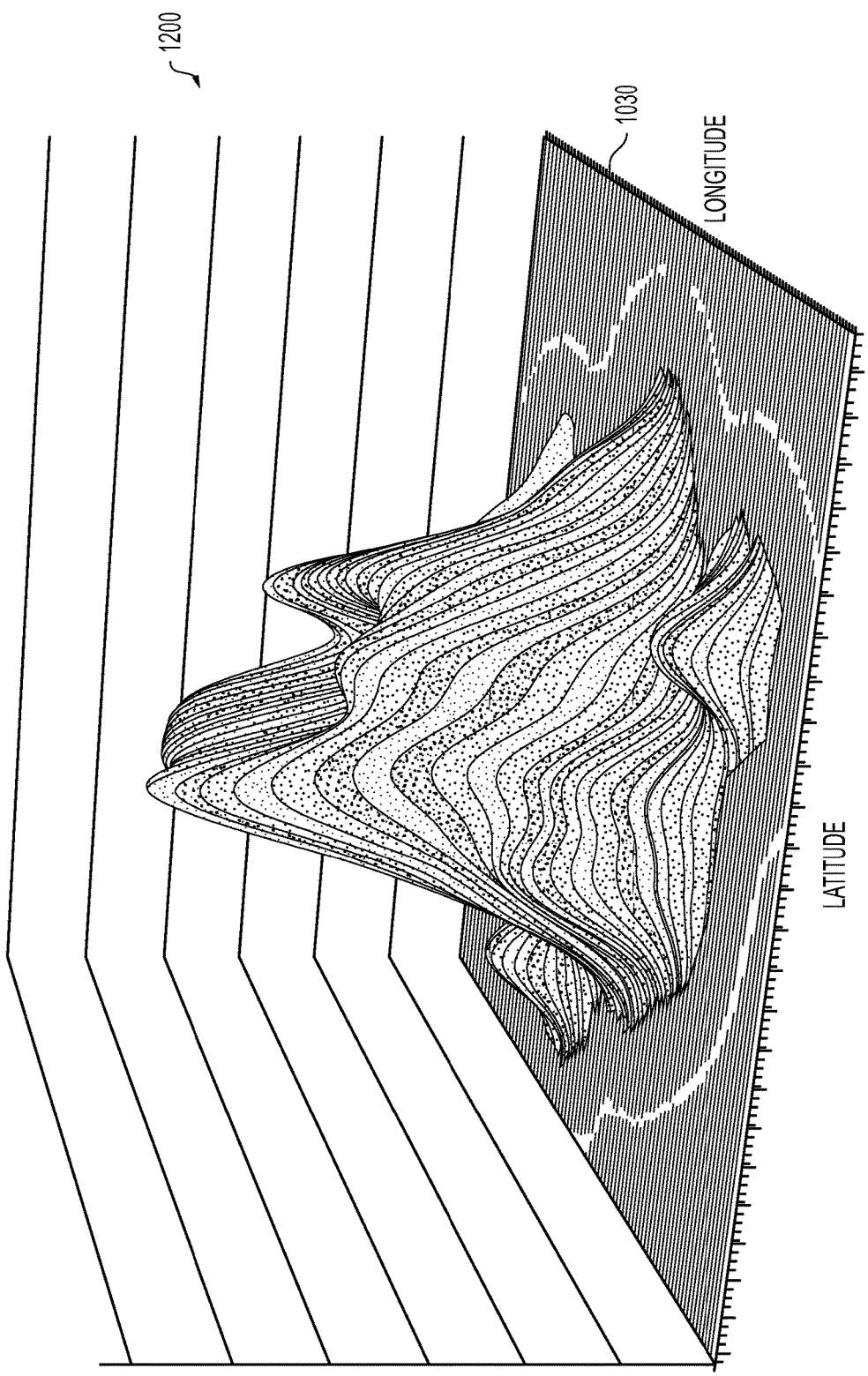

FIGS. 10-13 show various examples of golf course holes with shot data superimposed thereon, in accordance with some embodiments of the present invention. FIGS. 10-12 illustrate examples of intermediate steps or operations that may be utilized with embodiments of the present invention in order to form target maps or target zones.

In the example of FIG. 10, a collection of tee shots 1020 are mapped against a graphical representation of a fairway 1010—for instance, the shots 1020 may be filtered to include the shots that resulted in a score of par or better, for a handicap and gender selected by the user, after erroneous data has been filtered out. In FIG. 11, a bounding box 1030 is positioned about these shots 1020 to form a cluster so that a distribution or spatial representation of the shot data can be calculated.

As shown in FIG. 12, in one example, a distribution 1200 of the shots 1020 collected in FIG. 11 is calculated showing the spatial or positional frequency of the shots. Note that in one example, the bounding box 1030 of FIG. 11 is maintained in FIG. 12, and the data corresponding to the shots within the bounding box 1030 are used in calculating the statistical distribution of the shots. In one example, the distribution is a Gaussian density, such as a Kernel Density Estimator (KDE), and one such example of a KDE distribution is shown in FIG. 12. Other calculations can be used if desired, such as but not limited to, convex hull or any other calculation to determine spatial representations of the shot data.

Figure 13:
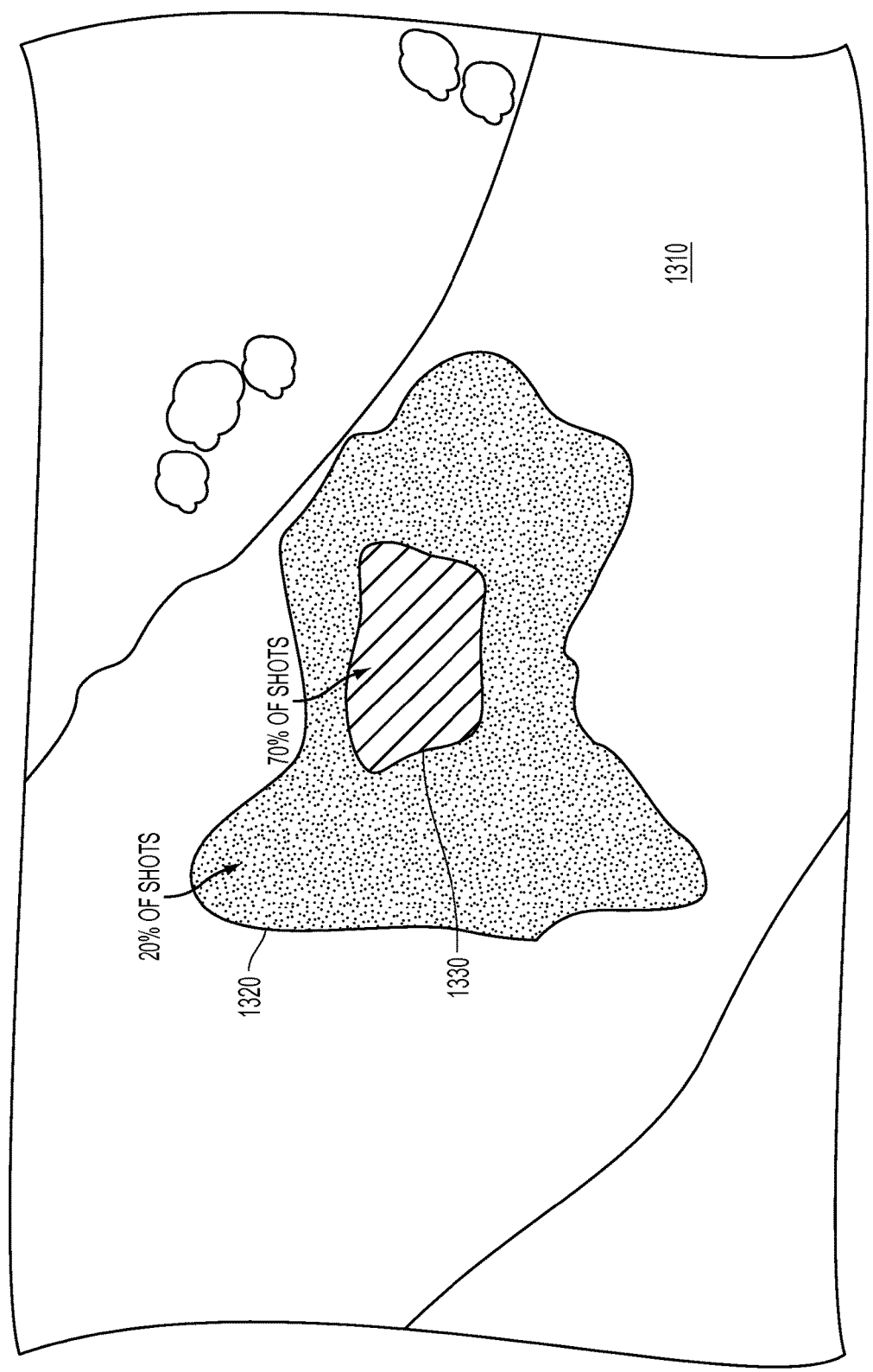

In the example of FIG. 13, a target map can be formed in one example by superimposing the distributions of FIG. 12 upon a graphical representation of a fairway 1310 at the corresponding locations on the fairway, and this image can be displayed to the user thereby indicating the target zones for viewing by the user. In this example, indicia for target zones are displayed as target regions and percentage indicators. Specifically, the display indicates 20% of par scores had shots that were positioned within a first target zone 1320 (shown with the dotted pattern in FIG. 13), and 70% of par scores had shots that landed within a second target zone 1330 (shown with a cross-hatch pattern in FIG. 13). Accordingly, a player would seek to hit a shot within the first target zone 1320 or second target zone 1330, and preferably within the second target zone 1330 if possible in order to increase their chance of scoring par or better on the hole. In one example of an embodiment of the present invention, the display presented on the user's device of the distributions of shots on the fairway 1310 or other part of the golf course can include color displays (such as but not limited to "heat maps") to show different percentages or differing amounts of the shot distributions, in one example.

Figure 14:
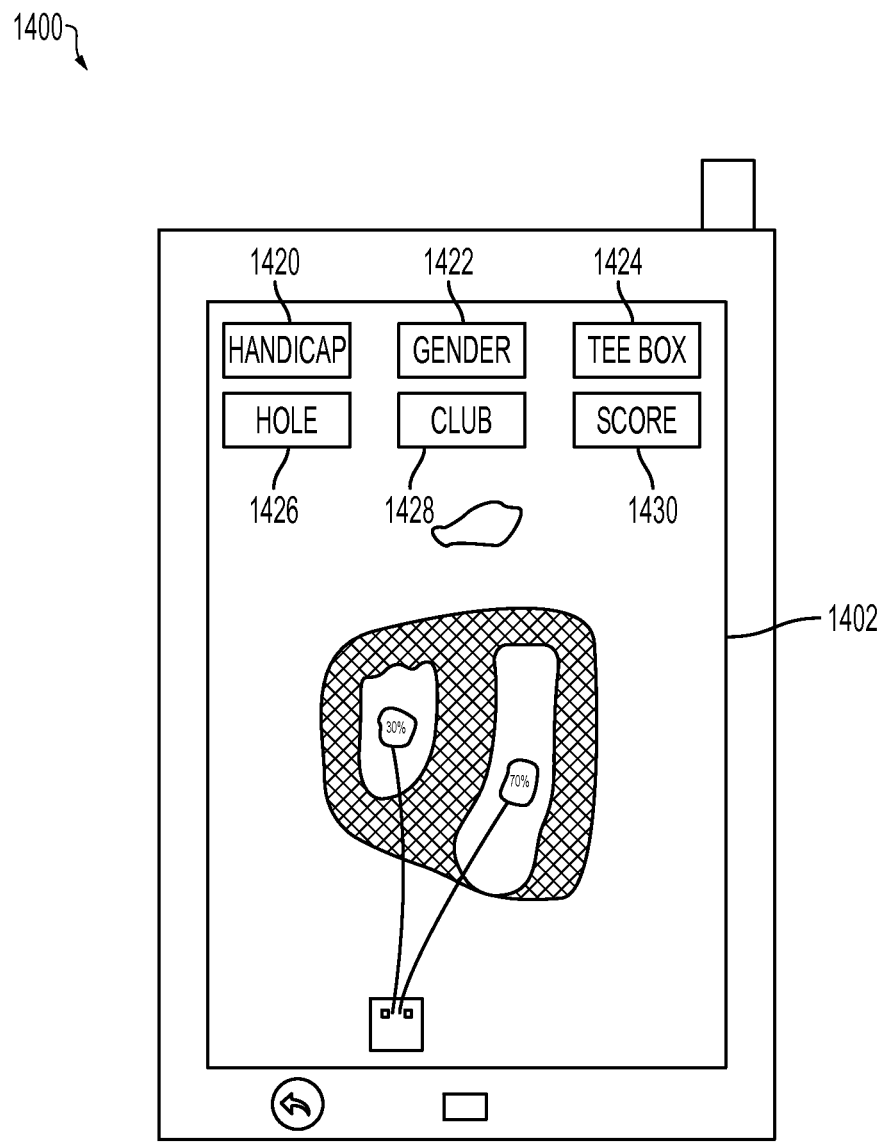
FIG. 14 illustrates an example of a mobile device having a display screen with target shot zone locations information for a golfer, in accordance with one embodiment of the present invention.

FIG. 14 illustrates an example of a mobile device 1400 having a (touchscreen) display 1402 with target shot zone locations information for a golfer, in accordance with one embodiment of the present invention. As mentioned above, the mobile device 1400 can include, but is not limited to, electronic devices such as smart phones, tablet computers, GPS devices, golf range finders, or other mobile electronic devices utilized by users such as golfers, golf instructors, course managers and other observers. In one example, the device 1400 may include a touchscreen display 1402 and may be provided with one or more controls for selecting the presentation of golf zone targets based on handicap (control 1420), gender (control 1422), tee-box (control 1424), golf hole (control 1426), club (control 1428), and score (control 1430). Other controls may be provided as desired such as controls to select the golf course, controls for navigation through an application, etc. These controls may initiate one or more of the processes or functions described herein.

Accordingly, it can be seen that embodiments of the present invention provide for target zones, target lines, target maps, or other target information to a golfer or observer through an electronic device, wherein the target zone/line/target data can be adjusted based on a desired result (such as par, birdie, bogey, etc.), handicap, tee-box, club selection, golfer's gender, or other variable.

While embodiments of the present invention have been described with reference to providing target maps, target zones, target lines, or other indications of targets, for use by a golfer in hitting tee shots for a golf hole, it is understood that embodiments of the present invention can also be utilized for providing targets for other shots during a round of golf, as desired, such as a second shot, an approach shot, a bunker shot, or other shots during play.

It should be appreciated that reference throughout this specification to "one embodiment" or "an embodiment" or "one example" or "an example" means that a particular feature, structure or characteristic described in connection with the embodiment may be included, if desired, in at least one embodiment of the present invention. Therefore, it should be appreciated that two or more references to "an embodiment" or "one embodiment" or "an alternative embodiment" or "one example" or "an example" in various portions of this specification are not necessarily all referring to the same embodiment. Furthermore, the particular features, structures or characteristics may be combined as desired in one or more embodiments of the invention.

It should be appreciated that in the foregoing description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed inventions require more features than are expressly recited in each claim. Rather, inventive aspects lie in less than all features of a single foregoing disclosed embodiment, and each embodiment described herein may contain more than one inventive feature.

While any methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

While the invention has been particularly shown and described with reference to embodiments thereof, it will be understood by those skilled in the art that various other changes in the form and details may be made without departing from the spirit and scope of the invention.

What is claimed is:

1. A computer-implemented method of producing a target map for a computing device having a display, the method comprising:
   determining a location of the computing device relative to a hole on a golf course using a global positioning service (GPS) device of the computing device;
   obtaining a set of golf shot data including shot location data from a plurality of users and associated with the hole on the golf course;
   calculating a subset of target locations, comprising filtering the shot location data of the set of golf shot data based on a target score for the hole, the target score received from a user operating the computing device;
   producing a target map using the subset of target locations; and
   displaying, using the display, a visual indicia of the target map overlaid on an image depicting at least a portion of the hole on the golf course.

2. The computer-implemented method of claim 1, wherein the visual indicia include a target line superimposed on the image.

3. The computer-implemented method of claim 1, wherein the visual indicia include a percentage indication that corresponds to a statistical frequency of shots that resulted in the target score.

4. The computer-implemented method of claim 1, wherein the set of golf shot data is associated with tee-shots for the hole on the golf course.

5. The computer-implemented method of claim 1, wherein:
   the GPS device is a first GPS device; and
   the set of golf shot data comprises geolocation data obtained using one or more of:
   a second GPS device; and
   cellular network locations services.

6. The computer-implemented method of claim 1, further comprising:
   receiving a club selection from the user; and
   determining a second subset of target locations that corresponds to shots performed using the club selection from the user.

7. The computer-implemented method of claim 1, further comprising:
   receiving a tee-box selection from the user; and
   determining a second subset of target locations that corresponds to shots initiated from the tee-box selection from the user.

8. The computer-implemented method of claim 1, further comprising:
   receiving an adjusted target score from the user; and
   computing an adjusted subset of target locations using the adjusted target score; and computing an adjusted target map using the adjusted subset of target locations.

9. The computer-implemented method of claim 1, further comprising:
receiving a handicap parameter from the user; and
determining a second subset of target locations using the handicap parameter.

10. The computer-implemented method of claim 1, further comprising:
displaying a club selection based on the target map.

11. A computer server for producing a target map comprising:
a processor;
memory storing computer-readable instructions that, when executed by the processor, cause the server to:
receive a location of a mobile device relative to a hole on a golf course determined using a global positioning service (GPS) device of the mobile device;
obtain a set of golf shot data from a database, the set of golf shot data including golf shot information from a plurality of users and associated with the hole on the golf course;
calculate a subset of target locations, comprising filtering the golf shot information based on a target score for the hole, the target score received from a user operating the computing device;
produce a target map using the subset of target locations; and
cause a display on the mobile device of a visual indicia of the target map overlaid on an image depicting at least a portion of the hole on the golf course.

12. The computer server of claim 11, wherein:
the computer server is configured to communicate with the mobile device via a computer network; and
golf data of the set of golf shot data includes location information associated with previous shots.

13. The computer server of claim 11, wherein golf data of the set of golf shot data includes one or more of:
a number of shots for the hole;
environmental conditions associated with a shot; and
handicap information associated with the user.

14. The computer server of claim 11, wherein the golf shot data was collected over multiple previous golf games and from multiple users.

15. A computer-implemented method of producing a target map for a computing device, the method comprising:
determining a location of the computing device relative to a hole on a golf course using a global positioning service (GPS) device of the computing device;
obtaining a set of golf shot data including golf shot information from a plurality of users and associated with the hole on the golf course;
computing a filtered set of golf shot data by removing inaccurate data from the set of golf shot data;
calculating a subset of target locations, comprising further filtering the filtered set of golf shot data based on a handicap or a handicap range received from a user operating the computing device;
producing a target map using the subset of target locations; and
displaying a visual indicia of the target map overlaid on an image depicting at least a portion of the hole on the golf course.

16. The computer-implemented method of claim 15, wherein filtering the set of golf shot data is further based on a club type corresponding to a club used to drive from a tee-box on the hole.

17. The computer-implemented method of claim 15, wherein filtering the set of golf shot data is further based on a club type corresponding to a club selected by the user for a current shot.

18. The computer-implemented method of claim 15, wherein the target score is par or better.

19. The computer-implemented method of claim 15, wherein the visual indicia include a percentage indication that corresponds to a statistical frequency of shots that resulted in the target score.

20. The computer-implemented method of claim 15, wherein the visual indicia include multiple target zones overlaid on the image.

* * * * *